United States Patent
Hassan et al.

(10) Patent No.: US 7,678,435 B2
(45) Date of Patent: Mar. 16, 2010

(54) ON-LINE MAKING OF POWDER-FREE RUBBER GLOVES

(75) Inventors: Noorman Bin Abu Hassan, Shah Alam (MY); David Mark Lucas, Petaling Jaya (MY); Hisam Ibrahim, Selangor (MY)

(73) Assignee: Ansell Healthcare Products LLC, Red Bank, NJ (US)

( * ) Notice: Subject to any disclaimer, the term of this patent is extended or adjusted under 35 U.S.C. 154(b) by 777 days.

(21) Appl. No.: 10/599,348

(22) PCT Filed: Apr. 16, 2004

(86) PCT No.: PCT/US2004/011799

§ 371 (c)(1),
(2), (4) Date: Sep. 26, 2006

(87) PCT Pub. No.: WO2005/110749

PCT Pub. Date: Nov. 24, 2005

(65) Prior Publication Data

US 2009/0139012 A1 Jun. 4, 2009

(51) Int. Cl.
  B29D 22/00 (2006.01)
  B29D 23/00 (2006.01)
  B32B 1/08 (2006.01)
  B65D 39/00 (2006.01)

(52) U.S. Cl. .............. 428/36.8; 428/423.9; 428/424.2; 428/424.8; 428/425.5; 428/451; 428/438; 428/492; 428/516; 428/35.2; 428/35.7; 428/35.9; 428/446; 428/447; 428/448; 428/327; 2/168; 2/161.7

(58) Field of Classification Search .............. 428/423.9, 428/424.2, 424.8, 425.5, 451, 438, 492, 516, 428/35.2, 35.7, 35.9, 36.8, 446, 447, 448, 428/327; 2/168, 161.7
See application file for complete search history.

(56) References Cited

U.S. PATENT DOCUMENTS

| 4,143,109 A | 3/1979 | Stockum |
| 4,310,928 A | 1/1982 | Joung |
| 4,597,108 A | 7/1986 | Momose |
| 5,088,125 A | 2/1992 | Ansell et al. |
| 5,284,607 A | 2/1994 | Chen |
| 5,335,373 A | 8/1994 | Dangman et al. |
| 5,534,350 A | 7/1996 | Liou |

(Continued)

OTHER PUBLICATIONS

EP Search Report for Appln. No. 04821994.3 (PCT/US2004/011799), (Apr. 22, 2009), 4 pgs.

Primary Examiner—Michael C Miggins
(74) Attorney, Agent, or Firm—Diehl Servilla LLC

(57) ABSTRACT

A powder-free medical glove having a first surface of a powder-free coagulant and a second surface with a polymer coating to ease donning. The powder-free coagulant on the first surface comprises micronized high-density polyethylene, a micro-emulsion of amino silicone, a dimethicone emulsion, calcium salts, an ethoxylated acetylenic diol surfactant and a cellulose thickener. The medical gloves are made in an on-line process of making latex articles that involves dipping hand-shaped formers into the coagulant before dipping them into the latex. The gloves are thereafter coated with a polymer to improve donnability before removal from the formers. The novel coagulant formulation permits easy removal of the articles from the formers, eases double-donning of gloves and eliminates the need for off-line processing.

18 Claims, 1 Drawing Sheet

U.S. PATENT DOCUMENTS

| | | |
|---|---|---|
| 5,570,475 A | 11/1996 | Nile et al. |
| 5,612,083 A | 3/1997 | Haung et al. |
| 5,674,818 A | 10/1997 | Garcia et al. |
| 5,742,943 A | 4/1998 | Chen |
| 5,985,955 A | 11/1999 | Bechara et al. |
| 6,016,570 A | 1/2000 | Vande Pol et al. |
| 6,019,922 A | 2/2000 | Hassan et al. |
| 6,075,081 A | 6/2000 | Nile et al. |
| 6,195,805 B1 | 3/2001 | Bourne et al. |
| 6,378,137 B1 | 4/2002 | Hassan et al. |
| 6,391,409 B1 | 5/2002 | Yeh et al. |
| 6,638,587 B1 | 10/2003 | Wang et al. |

Polymer Coated Latex Glove Process Flowchart

ON-LINE MAKING OF POWDER-FREE RUBBER GLOVES

FIELD OF THE INVENTION

The present invention relates to a medical glove and an on-line process of making powder-free synthetic and natural rubber latex gloves by dipping and to the methods and materials used in manufacturing these gloves. This invention particularly relates to synthetic and natural latex medical gloves and other latex articles employing a powder-free coagulant during manufacturing.

BACKGROUND OF THE INVENTION

Gloves fabricated from elastomeric materials such as natural rubber latex and synthetic latex have encountered a variety of problems. An important criterion for medical gloves is that they conform tightly to the hand of the wearer. Natural rubber, with its inherent high coefficient of friction, makes glove donning difficult. To solve this problem, conventional medical gloves use a lubricant on the inner surface to ease glove donning. This lubricant also serves to ease removal of the glove from the hand-shaped former used in manufacturing. Commonly, the lubricant is in powder form and is generally of an absorbent nature; for example, starch powder is commonly used. There have, however, been doubts in the medical community about using loose dusting powder in gloves used for surgical procedures. As a result, many efforts have been made to reduce or eliminate the use of loose powder to facilitate the donning of medical gloves by developing various powder-free methods to improve donning properties.

Synthetic latex and natural rubber gloves are commonly fabricated by a process of first dipping a hand-shaped former, or mandrel, into a powdered coagulant bath, dipping the former into a latex or natural rubber bath, and finishing with a leaching and drying process. Frequently, gloves made by this process result in gloves that have a tendency to stick to the former after drying. Upon stripping the glove from the former, gloves fabricated by this process often tear and stick together.

In commercially made gloves, the coagulant bath includes a powder of mineral origin to provide antiblocking properties on the former surface. Antiblocking powders prevent the two layers of the glove from sticking to one another. The powder is usually calcium carbonate or talc, as these powders can withstand the high temperatures (100-130° C.) used in latex glove fabrication. On the outside surface, a starch or other powder layer is applied by dipping a former with a cured latex glove into a starch slurry bath. Alternatively, the cured latex glove may be coated with a synthetic polymer coating to impart antiblocking properties.

There are also disclosures relating to off-line chlorination, washing and siliconization processes for making powder-free medical gloves. These processes remove talc and cornstarch powder residues, reduce tackiness and improve glove donnability. These processes, however, are usually labor-intensive and use large amounts of water, making them very expensive. Moreover, chlorination can result in poor physical strength, discoloration and poor aging characteristics of the glove. In some situations, chlorination can pose storage and environmental hazards.

The making of powder-free medical gloves using a chlorination process, polymer coating methods, or a combination of both, are disclosed in U.S. Pat. Nos. 6,195,805; 5,674,818; 5,612,083; 5,570,475; 5,284,607; 5,088,125; 4,597,108 and 4,143,109. There are, however, few disclosures describing the malting of powder-free gloves without post-processing, or off-line, steps such as chlorination, washing and/or siliconization. Among these few disclosures are U.S. Pat. Nos. 6,075,081; 5,534,350 and 4,310,928.

U.S. Pat. No. 6,075,081 to Nile discloses a powder-free coagulant for use in latex dipping processes comprising a salt-stable dispersion of a polychloroprene rubber and an inorganic metal salt. The coagulant of this disclosure may also contain a powder-free release agent comprising a polypropylene wax emulsion and a cationic surfactant to aid release of the dipped article from the former.

U.S. Pat. No. 5,534,350 to Liou discloses an on-line process of making powder-free medical gloves using a polyurethane polymer in the coagulant that acts as a waterproof lubricating layer to ease stripping the glove from the ceramic former. A coat of polyurethane polymer on the inside of the glove improves donning.

U.S. Pat. No. 4,310,928 to Joung discloses coating a glove former with a coagulant containing a lipo compound and a surfactant in a dispersion. These materials stay with the glove after it is stripped from the former, thereby providing a release surface for the glove.

Additionally, U.S. Pat. No. 6,378,137 to Hassan et al. discloses the making of a powder-free medical glove that uses an antiblocking composition of a polymer or copolymer mixed with a micronized high-density polyethylene material and a wax. This composition makes the glove easier to don. However, the glove remains only substantially free of powder in the finished product and requires treatment with a silicone emulsion/wax mixture in off-line processing. U.S. Pat. No. 6,019,922 to Hassan et al. discloses an additional method for making powder-free medical gloves that includes a silicone treatment on the outside surface of the glove and an antiblocking composition on the inside surface of the glove. The antiblocking composition of this reference is comprised of a polymer or copolymer, a micronized high-density polyethylene material and wax. To manufacture the gloves of this reference, however, the manufacturer must rinse the finished glove to remove remaining coagulant powder. This rinsing process is not perfected and results in gloves that are only substantially free of powder, rather than completely free of powder. The glove process of this disclosure also requires off-line processing, including treatment of the gloves with a silicone solution to produce a finished product.

It is therefore desirable to have a powder-free, non-tacky glove with good donning properties that can be easily stripped from a glove former following fabrication. It is also desirable that this powder-free glove require only a minimal number of processing steps, most preferably requiring no off-line processing. It is therefore desirable to provide a novel way of producing powder-free synthetic latex or natural rubber dipped gloves that solves the foregoing problems of off-line processing. Embodiments of the present invention provide a novel coagulant composition that eliminates off-line processing because no calcium carbonate is used, and, as a result, off-line chlorination, washing and siliconization are eliminated. The resulting process lowers the cost of production and yields a completely powder-free glove.

SUMMARY OF THE INVENTION

According to one embodiment of the present invention, a powder-free coagulant composition is used with synthetic polychloroprene latex in an on-line process to make gloves that are powder-free and do not require any off-line processing. In particular, the process used to make these gloves includes in one embodiment dipping a hand-shaped former into a novel coagulant composition comprising micronized high-density polyethylene, a micro-emulsion of amino silicone, a dimethicone emulsion, calcium salts, a surfactant and a cellulose thickener before dipping the former into a natural rubber or synthetic latex composition.

In one embodiment, the method of preparing the article of the present invention includes the steps of: dipping a shaped, preheated former into an aqueous powder-free solution comprising an aqueous, salt-stable solution of micronized high-density polyethylene, a micro-emulsion of amino silicone, a dimethicone emulsion, an acetylenic diol surfactant and an inorganic metal salt; dipping the former in a dispersion of a polychloroprene latex to form a gelled latex film and to create a tack-free surface for the article; leaching the gelled latex film; priming the gelled latex film with a low-salt solution; dipping the gelled latex film into a polymer coating; drying the polymer coating; curing the formed rubber articles on the former; and stripping the cured tack-free article from the former.

The polymer coating on the inside of the glove can be acrylic- or polyurethane-based and is to be applied before curing. This coating may be further enhanced by dipping the cured glove into a silicone dip before removing the glove from the former. This polymer coating with optional silicone dip will serve to facilitate donning of the glove.

In accordance with the principles of this invention, a method of producing powder-free rubber or latex articles, in particular articles produced by conventional dipping processes, such as medical and surgical gloves, condoms and catheters, is provided.

DETAILED DESCRIPTION OF THE INVENTION

Figure 1:
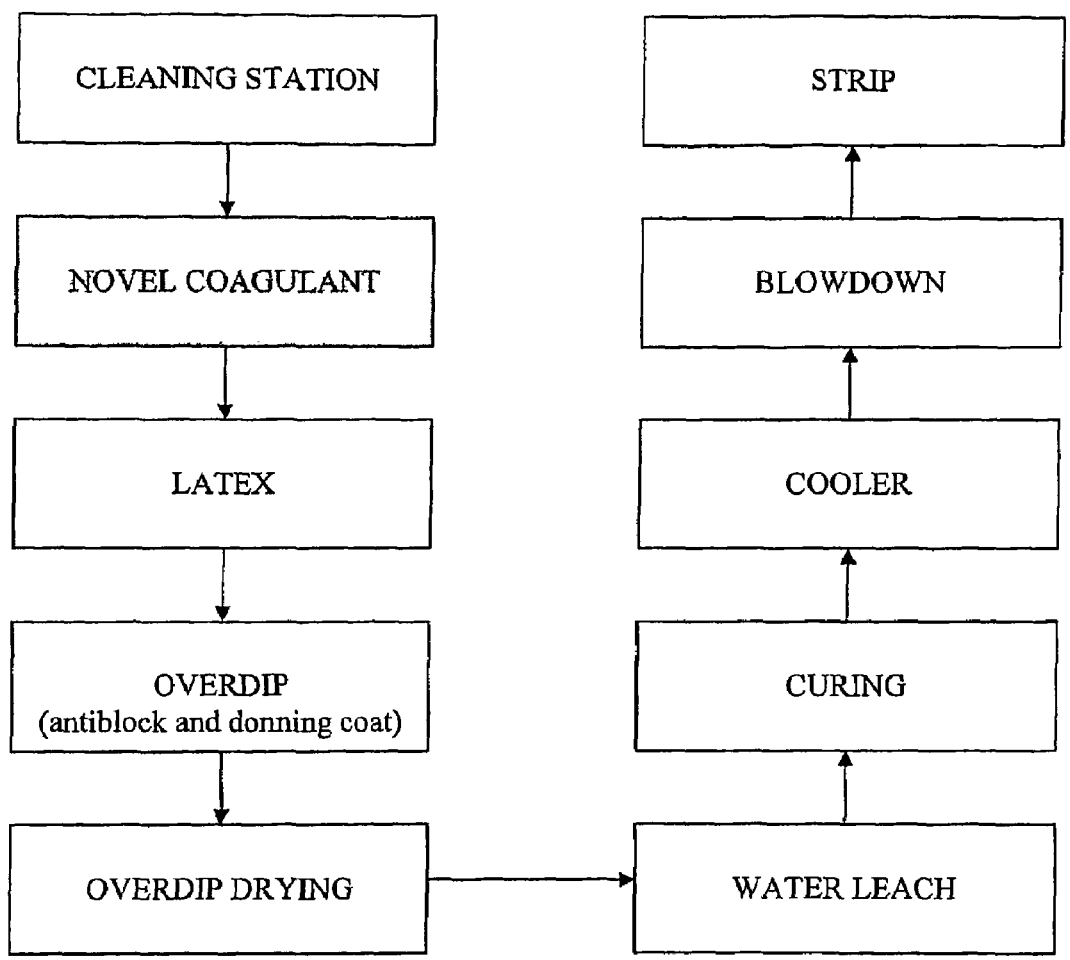
FIG. 1 illustrates a flowchart of a dipping process for the on-line making of powder-free gloves in accordance with an embodiment of the invention.

Embodiments of the present invention provide the ability to vary the grip properties of a synthetic latex or natural rubber article, particularly a medical glove, according to the compositional amount of dimethicone emulsion incorporated into the novel coagulant formulation. In one embodiment, the novel coagulant formulation, at termination of the manufacturing process, will be on the outside surface of the glove, creating a slippery surface that will improve the ability to double don the glove, or wear two pairs of gloves, one atop the other.

Articles, medical gloves in particular, produced according to embodiments of the present invention are formed by dipping a heated hand-shaped former (smooth, patterned or textured) into a novel coagulant composition. The novel coagulant composition includes micronized high-density polyethylene, a micro-emulsion of amino silicone, a dimethicone emulsion, calcium salts, an ethoxylated acetylenic diol surfactant and a cellulose thickener. The coagulant-coated former is then removed from the coagulant tank and dipped into a synthetic or natural elastomeric latex dispersion to form a gelled latex film. Preferably, the latex is a polychloroprene latex. The gelled latex film is then leached and dipped into a polymer coating.

According to one embodiment of the present invention, the gelled latex gloves are next cured on the former before stripping the cured tack-free article from the former. In another embodiment of the present invention, the gelled latex gloves are cured on the former and then dipped into a silicone dip before removing the glove from the former. The polymer coating with silicone dip as described in this embodiment of the invention will further ease donning of the glove.

Preferably, the dimethicone-based silicone emulsion is prepared from polydimethylsiloxane fluid having a viscosity ranging from about 10,000 to about 100,000 centistokes at 25° centigrade and an average molecular weight of between about 62,700 and about 116,500.

Emulsions prepared from the dimethicone fluids within the above viscosity range, when incorporated into the novel coagulant formulation, will provide a relatively small viscosity fluctuation over a wide temperature range. The emulsions will provide good thermal/oxidative stability, chemical inertness and resistance to breakdown under mechanical shear. They will also present good antifriction properties to the exposed elastomer surface of the glove in contact with the novel coagulant, easing removal of the gloves from the formers during manufacturing.

Several emulsions and fluids prepared from dimethicone fluids are commercially available. For example, an emulsion prepared from a dimethicone fluid with a viscosity of about 10,000 centistokes is marketed by GE Silicones, USA, under the trade name SM 2140. A fluid prepared from the same base materials is marketed by GE Silicones, USA, under the trade name VISCASIL 10M. An emulsion prepared from dimethicone fluid with a viscosity of about 100,000 centistokes is marketed by GE Toshiba Silicones Co. Ltd, Japan, under the trade name XS65-135891. A fluid prepared from the same base materials is marketed by GE Toshiba Silicones Co. Ltd, Japan under the trade name TSF 451-10M. Dimethicone fluids ranging from about 10,000 to about 100,000 centistokes are classified as high-viscosity fluids and marketed under the trade name 200 FLUID by Dow Corning Corporation. Emulsions can also be prepared from a mixture of dimethicone and cyclomethicone; an example of such an emulsion is marketed by Dow Corning Corporation under the trade name DOW CORNING Q2-1803.

The use of a micro-emulsion of amino silicone is designed to produce a silky texture on the glove surface and enhance the softness of the gloves. A micro-emulsion of amino silicone is available under the trade name SOFTEX 5850, marketed by Kao Industrial (Thailand) Company Ltd.

The use of micronized high-density polyethylene may act as an anchor to enhance coagulant film coverage as well as to facilitate stripping the gloves from the hand-shaped formers. The micronized high-density polyethylene also provides antifriction and antiblocking properties to the outside surface of the glove (the side of the glove in contact with the coagulant during dipping process). The range of effective melting points for high-density polyethylene is typically between about 100 and about 130° C. The average particle size of micronized high-density polyethylene is typically between about 3 and about 12 microns.

Non-ionic acetylenic diol surfactant is normally used as a wetting agent for the coagulant and cellulose thickener is preferred to thicken the coagulant.

Embodiments of the present invention will now be further described in the following examples and is accompanied by a flowchart for producing such articles (FIG. 1) according to embodiments of the invention.

EXAMPLE 1

A ceramic bisque former was heated to 60-70° C. and then dipped into a 25-35° C. antiblocking coagulant dispersion for approximately 5-10 seconds. The coagulant dispersion contained:

|  | Weight % |
|---|---|
| Calcium nitrate | 18% |
| Micronized HDPE | 1% |
| Micro-emulsion of amino silicone | 1% |
| Cellulose thickener | 0.2% |
| Acetylenic diol surfactant | 0.3% |
| Water | 79.5% |

In the formulation of Example 1, the micronized HDPE was added as a 20% dispersion, the micro-emulsion of amino silicone was supplied as a 20 to 22% emulsion, the cellulose thickener was diluted to a 1% solution and the acetylenic diol surfactant was added as supplied. After being dipped into the coagulant dispersion, the ceramic former was slowly pulled out of the coagulant dispersion and rotated to uniformly distribute the coagulant over the former surface. The former was then moved to an oven heated to 90° C. for about 90 seconds to dry the coagulant. After drying, the ceramic former was dipped into a polychloroprene latex dispersion for about 20 to 30 seconds. This polychloroprene latex dispersion contains 40% dry polymer and was maintained at 25° C. After polychloroprene latex was deposited on the former, it was turned and lifted, and then heated in an oven at 75° C. for about 60 seconds. The gelled polychloroprene latex was next leached at between 40 and 60° C. for about 180 seconds. The polychloroprene polymer gel on the ceramic former was then dipped into a 1 to 2% primer of salt solution before being dipped into either a polyurethane or an acrylic coating solution. The ceramic former was then gradually dried at between 110 and 140° C. for 35 minutes. The former was then cooled before the glove was stripped from it. The former can be reused in further production cycles by rinsing it in acid and then in water. The former was also easily cleaned with standard cleaning agents used in glove dipping.

A glove that was dipped using the powder-free coagulant formulation of Example 1 was free from thin patches and stripped easily from the ceramic former. The glove grip was satisfactory and double gloving was satisfactory with the same type and size of gloves. The polychloroprene glove has powder-free attributes with a powder level of less than 2 mg per glove.

EXAMPLE 2

In accordance with Example 1, gloves were produced in a similar procedure with the exception of the composition of the antiblocking coagulant. The antiblocking coagulant dispersion for this example contained:

|  | Weight % |
| --- | --- |
| Calcium nitrate | 18% |
| Micronized HDPE | 1% |
| Micro-emulsion of amino silicone | 1% |
| Dimethicone/cyclomethicone emulsion | 0.1% |
| Cellulose thickener | 0.2% |
| Acetylenic diol surfactant | 0.3% |
| Water | 79.4% |

In this example, the dimethicone/cyclomethicone blend emulsion added was supplied as a 60% emulsion. The gloves produced in this example dipped well with no thin patches and stripped easily from the ceramic former. The glove grip was less aggressive than the glove produced in Example 1, and double gloving was good using the same type and size of gloves. The polychloroprene glove has powder-free attributes with a powder level of less than 2 mg per glove.

EXAMPLE 3

In accordance with Example 1, gloves were produced in a similar procedure with the exception of the composition of the antiblocking coagulant. The antiblocking coagulant dispersion for this example contained:

|  | Weight % |
| --- | --- |
| Calcium nitrate | 18% |
| Micronized HDPE | 1% |
| Micro-emulsion of amino silicone | 1% |
| Dimethicone/cyclomethicone emulsion (100,000 centistokes) | 0.1% |
| Cellulose thickener | 0.2% |
| Acetylenic diol surfactant | 0.3% |
| Water | 79.4% |

In this example, the dimethicone/cyclomethicone blend emulsion supplied was manufactured from a 100,000 centistokes polydimethyl siloxane fluid viscosity measured at 25° C. The gloves dipped well with no thin patches and stripped easily from the ceramic former. The glove grip was more slippery than any of the previous examples and double gloving was excellent using the same type and size of gloves. The polychloroprene glove has powder-free attributes with a powder level of less than 2 mg per glove.

EXAMPLE 4

In accordance with Example 1, gloves were produced in a similar procedure with the exception of the composition of the antiblocking coagulant. The antiblocking coagulant dispersion for this example contained:

|  | Weight % |
| --- | --- |
| Calcium nitrate | 18% |
| Micronized HDPE | 1% |
| Micro-emulsion of amino silicone | 2% |
| Dimethicone emulsion (10,000 centistokes) | 0.2% |
| Cellulose thickener | 0.2% |
| Acetylenic diol surfactant | 0.3% |
| Water | 78.3% |

In this example, the dimethicone emulsion supplied was manufactured from a polydimethyl siloxane fluid with a viscosity of 10,000 centistokes measured at 25° C. The gloves dipped well with no thin patches and stripped easily from the ceramic former. The glove grip was less slippery than that of the gloves produced in Example 3 and less aggressive than that of the gloves in Examples 1 and 2. Double gloving of the same size and type of gloves was excellent. The polychloroprene glove has powder-free attributes with a powder level of less than 2 mg per glove.

EXAMPLE 5

In accordance with Example 1, gloves were produced in a similar procedure with the exception of the composition of the antiblocking coagulant. The antiblocking coagulant dispersion for this example contained:

|  | Weight % |
| --- | --- |
| Calcium nitrate | 18% |
| Micronized HDPE | 1% |
| Micro-emulsion of amino silicone | 2% |
| Dimethicone emulsion (10,000 centistokes) | 0% |
| Cellulose thickener | 0.2% |

-continued

| | Weight % |
|---|---|
| Acetylenic diol surfactant | 0.3% |
| Water | 78.5% |

EXAMPLE 6

In accordance with Example 1, gloves were produced in a similar procedure with the exception of the composition of the antiblocking coagulant. The antiblocking coagulant dispersion for this example contained:

| | Weight % |
|---|---|
| Calcium nitrate | 18% |
| Micronized HDPE | 1% |
| Micro-emulsion of amino silicone | 2% |
| Dimethicone emulsion (10,000 centistokes) | 0.2% |
| Cellulose thickener | 0.2% |
| Acetylenic diol surfactant | 0.3% |
| Water | 78.3% |

EXAMPLE 7

In accordance with Example 1, gloves were produced in a similar procedure with the exception of the composition of the antiblocking coagulant. The antiblocking coagulant dispersion for this example contained:

| | Weight % |
|---|---|
| Calcium nitrate | 18% |
| Micronized HDPE | 1% |
| Micro-emulsion of amino silicone | 2% |
| Dimethicone emulsion (10,000 centistokes) | 0.4% |
| Cellulose thickener | 0.2% |
| Acetylenic diol surfactant | 0.3% |
| Water | 78.1% |

The grip properties produced by using the different levels of dimethicone in Examples 5-7 are tabulated in Table 1. The grip properties were determined on a coefficient of friction tester made by RJ Harvey Instrument Corporation, USA.

As can be seen in Table 1, by varying the dimethicone level of the coagulant, the friction properties on the coagulant side of a polychloroprene rubber surface can be varied according to the grip property requirements. All the polychloroprene gloves in Examples 5-7 have powder-free attributes with powder levels of less than 2 mg per glove.

EXAMPLE 8

In accordance with Example 1, gloves were produced in a similar procedure with the exception of the composition of the antiblocking coagulant and the substitution of natural rubber latex for the polychloroprene latex dispersion of Example 1. The antiblocking coagulant dispersion for this example was the same as that used in Example 4.

Natural rubber gloves dipped well with no thin patches and stripped easily from the ceramic former. The glove grip was more aggressive than that of any of the gloves from Examples 1-7. Rubber friction properties as measured using an R J Harvey Instrument show a Metal over Rubber (MR) value of approximately 250 gmf, correlating to a COF value of 1.26. The natural rubber glove has powder-free attributes with a powder level of less than 2 mg per glove.

EXAMPLE 9

The procedure for preparation of coagulant and production of gloves was similar to Example 8 with the exception of the coagulant composition. The antiblocking coagulant dispersion for this example contained:

| | Weight % |
|---|---|
| Calcium nitrate | 18% |
| Micronized HDPE | 2.5% |
| Micro-emulsion of amino silicone | 2.5% |
| Dimethicone emulsion (either 10,000 or 100,000 centistokes) | 0.4% |
| Cellulose thickener | 0.2% |
| Acetylenic diol surfactant | 0.3% |
| Water | 76.1% |

The natural rubber gloves produced from the formulation of this example dipped well with no thin patches and stripped easily from the ceramic former. The glove grip was less aggressive than that seen in gloves produced using the formulation of Example 7. Double gloving of the same size and type of gloves was satisfactory. Rubber friction properties, as

TABLE 1

| Rubber friction properties measured on coagulant side | Dimethicone level | | | | | |
|---|---|---|---|---|---|---|
| | Example 5 0% Dimethicone | | Example 6 0.2% Dimethicone | | Example 7 0.4% Dimethicone | |
| | Gram Force (gmf) | Coefficient of Friction (COF) | Gram Force (gmf) | Coefficient of Friction (COF) | Gram Force (gmf) | Coefficient of Friction (COF) |
| Metal over Rubber | 229 182-318 | 1.15 0.91-1.59 | 187 142-242 | 0.94 0.71-1.21 | 144 115-208 | 0.72 0.58-1.04 |
| Rubber over Rubber | 152 157-266 | 0.76 0.79-1.33 | 135 119-162 | 0.68 0.60-0.81 | 121 112-145 | 0.61 0.56-0.73 | measured using an R J Harvey Instrument, show an MR value of approximately 135 gmf or COF value of 0.68. The natural rubber gloves from this example have powder-free attributes with a powder level of less than 2 mg per glove.

While the invention has been described in conjunction with specific embodiments thereof, it is evident that alternatives, modifications and variations will be apparent to those skilled in the art in light of the foregoing description. Accordingly, it is intended to embrace all such alternatives, modifications and variations as fall within the spirit and broad scope of the appended claims.

The invention claimed is:

1. A powder-free elastomeric article, the article comprising:
    an elastomeric material having a first surface and a second surface;
    the first surface of the elastomeric material coated with a powder-free coagulant coating;
    the powder-free coagulant composition comprising:
        micronized high-density polyethylene;
        a micro-emulsion of amino silicone;
        a dimethicone emulsion;
        an ethoxylated acetylenic diol surfactant; and
        a cellulose thickener; and
    the second surface of the elastomeric material coated with a polymer coating wherein said article is a glove.

2. The article of claim 1 wherein the micro-emulsion of amino silicone includes mixed particles ranging in size from about 1 about 100 microns.

3. The article of claim 1 wherein that the coagulant composition comprises a total solids content of the following:
    between about 10% and about 30% calcium salts;
    between about 0.1% and about 3% micronized HDPE;
    up to about 1% of dimethicone emulsion;
    between about 0.1% and about 3 micro-emulsion of amino silicone; and
    between about 0.1% and about 0.5% non-ionic acetylenic diol surfactant.

4. The article of claim 1, wherein the polymer coating comprises a polyurethane-based coating or an acrylic coating.

5. The article of claim 1, wherein the article has an extractable powder level of less than 2 mg and has powder-free attributes.

6. The article of claim 1 wherein the elastomeric material is selected from the group consisting of polychloroprene, natural rubber, synthetic polyisoprene, carboxylated acrylonitrile butadiene and polyurethane.

7. The article of claim 6 wherein the second surface is halogenated.

8. The article of claim 1, wherein the first surface forms an outside surface of the article and the second layer forms an inside surface of the article.

9. The article of claim 8 comprising a glove, wherein the outside surface of the glove is in direct contact with an inside surface of a double donned glove enabling easy double donning.

10. The article of claim 8 comprising a glove, wherein the inside surface of the glove is in direct contact with skin when donned.

11. The article of claim 8 wherein the outside surface of the glove comprises a polychloroprene latex has a metal over rubber coefficient of friction in the range from about 0.58 to about 1.21.

12. The article of claim 8 wherein the outside surface of the glove comprises a polychloroprene latex has a rubber over rubber coefficient of friction in the range from about 0.56 to about 0.81.

13. The article of claim 8 wherein the outside surface of the glove comprises a natural rubber latex has a metal over rubber coefficient of friction measuring about 1.26.

14. The article of claim 8 wherein the outside surface of the glove comprises a natural rubber latex has a metal over rubber coefficient of friction measuring about 0.68.

15. The article of claim 1, wherein the dimethicone emulsion comprises dimethicone and cyclomethicone.

16. The article of claim 15, wherein the dimethicone in combination with a cyclomethicone is emulsified from a polydimethylsiloxane fluid source with a viscosity ranging from about 10,000 to about 100,000 centistokes.

17. The article of claim 15, wherein the dimethicone and the cyclomethicone is obtained from a polydimethylsiloxane fluid source with a viscosity of about 100,000 centistokes.

18. A powder-free elastomeric glove comprising:
    an elastomeric material having a first surface and a second surface;
    the first surface of the elastomeric material forming an outside surface of the glove and being coated with a powder-free coagulant coating;
    the powder-free coagulant composition comprising:
        micronized high-density polyethylene;
        a micro-emulsion of amino silicone;
        a dimethicone emulsion;
        an ethoxylated acetylenic diol surfactant; and
    the second surface of the elastomeric material forming an inside surface of the glove and being coated with a polymer coating comprising a polyurethane-based coating or an acrylic coating;
    wherein the glove has an extractable powder level of less than 2 mg and has powder-free attributes.

* * * * *